(12) United States Patent
Pilu

(10) Patent No.: US 7,657,062 B2
(45) Date of Patent: Feb. 2, 2010

(54) SELF-CALIBRATION FOR AN EYE TRACKER

(75) Inventor: Maurizio Pilu, Bristol (GB)

(73) Assignee: Hewlett-Packard Development Company, L.P., Houston, TX (US)

( * ) Notice: Subject to any disclaimer, the term of this patent is extended or adjusted under 35 U.S.C. 154(b) by 679 days.

(21) Appl. No.: 11/087,400

(22) Filed: Mar. 23, 2005

(65) Prior Publication Data

US 2005/0225723 A1 Oct. 13, 2005

(30) Foreign Application Priority Data

Mar. 25, 2004 (GB) .................. 0406710.4

(51) Int. Cl.
G06K 9/00 (2006.01)
H04N 7/18 (2006.01)
G09G 5/00 (2006.01)
A61B 3/14 (2006.01)

(52) U.S. Cl. .................. 382/103; 382/117; 348/78; 345/8; 351/209

(58) Field of Classification Search ............. 382/103, 382/117; 345/8; 351/209, 212; 348/78
See application file for complete search history.

(56) References Cited

U.S. PATENT DOCUMENTS

| | | | | |
|---|---|---|---|---|
| 3,542,457 A * | 11/1970 | Ziegler et al. | ............. | 351/206 |
| 4,595,990 A * | 6/1986 | Garwin et al. | ............. | 708/141 |
| 5,231,674 A * | 7/1993 | Cleveland et al. | ............. | 382/117 |
| 5,345,281 A * | 9/1994 | Taboada et al. | ............. | 351/210 |
| 5,481,622 A | 1/1996 | Gerhardt et al. | | |
| 5,604,818 A * | 2/1997 | Saitou et al. | ............. | 382/128 |
| 5,726,916 A * | 3/1998 | Smyth | ............. | 702/151 |
| 5,751,260 A * | 5/1998 | Nappi et al. | ............. | 345/8 |
| 6,204,828 B1 * | 3/2001 | Amir et al. | ............. | 345/7 |
| 6,359,601 B1 * | 3/2002 | Maguire, Jr. | ............. | 345/7 |
| 6,381,339 B1 * | 4/2002 | Brown et al. | ............. | 382/100 |
| 6,568,809 B2 * | 5/2003 | Trajkovic et al. | ............. | 351/209 |
| 6,574,352 B1 * | 6/2003 | Skolmoski | ............. | 382/103 |
| 6,758,563 B2 * | 7/2004 | Levola | ............. | 351/209 |
| 6,798,443 B1 * | 9/2004 | Maguire, Jr. | ............. | 348/121 |

(Continued)

FOREIGN PATENT DOCUMENTS

EP  1403680 A1  3/2004

(Continued)

OTHER PUBLICATIONS

Machine Translation of WO 01/33323 obtained from European Patent Office Website.*

(Continued)

Primary Examiner—Brian P Werner
Assistant Examiner—Anthony Mackowey

(57) ABSTRACT

Automatic calibration of an eye tracking system involves capturing a plurality of eye measurements, wherein each eye measurement relates to a corresponding eye gaze position of a human eye; determining a set of statistics data from the plurality of eye gaze measurements; comparing the set of statistics of eye gaze measurements with a set of statistics relating to a plurality of pre-measured eye gaze positions of at least one person; and as a result of the comparison, determining a calibration correction factor which, when applied to the statistics of eye gaze measurements, gives an optimum match between the statistics of eye gaze measurements and the statistics of predetermined eye gaze positions.

19 Claims, 8 Drawing Sheets

U.S. PATENT DOCUMENTS

| | | | |
|---|---|---|---|
| 2003/0123027 A1* | 7/2003 | Amir et al. | 351/209 |
| 2004/0044293 A1* | 3/2004 | Burton | 600/544 |
| 2004/0101170 A1* | 5/2004 | Tisse et al. | 382/117 |
| 2004/0239509 A1* | 12/2004 | Kisacanin et al. | 340/575 |
| 2005/0024586 A1* | 2/2005 | Teiwes et al. | 351/209 |
| 2005/0073136 A1* | 4/2005 | Larsson et al. | 280/735 |
| 2005/0119642 A1* | 6/2005 | Grecu et al. | 606/5 |

FOREIGN PATENT DOCUMENTS

| | | |
|---|---|---|
| GB | 2177276 A | 3/1986 |
| WO | WO 01/33323 A2 | 3/2001 |

OTHER PUBLICATIONS

GB Search Report dated Aug. 11, 2004.

\* cited by examiner

SELF-CALIBRATION FOR AN EYE TRACKER

TECHNICAL FIELD

The present invention relates to calibration, and particularly although not exclusively, to the calibration of wearable computing entities and/or wearable cameras.

CLAIM TO PRIORITY

This application claims priority to copending United Kingdom utility application entitled, "SELF-CALIBRATION FOR AN EYE TRACKER," having serial no. GB 0406710.4, filed Mar. 25, 2004, which is entirely incorporated herein by reference.

BACKGROUND

It is known in several fields of computing, for example of the fields of wearable computers, and for computer user interfaces, that control of computers or computer activated devices can be achieved by monitoring human eye movements, including eye gaze direction.

Prior art eye tracking devices are known in the fields of psychological research. One such known device comprises a white screen having a predetermined pattern of dots, which a user views. An eye tracking device having a camera sensor tracks the user's eye movements when looking at the screen in front of the user, in order to calibrate the positioning of the eye tracking device and the user's eye within a three dimensional external coordinate system. However, such known eye tracking devices and calibration systems tend to be bulky and cumbersome, and typically, the camera sensor is positioned away from the user at a fixed position in a room.

Many conventional eye tracking devices use reference objects within a scene, that is within a field of view of a user in order to perform calibration of an eye tracking device. In general, a tracking device, such as a camera, can be placed in fixed relationship to an eye for which it collects tracking data, but the position of the eye with reference to the environment, or the position of the camera with reference to the environment will initially be unknown. For a tracking device and an eye in a three dimensional coordinate system, a calibration needs to be made to enable placement of the eye within the coordinate system, and to enable placement of the eye tracking device within the coordinate system.

A concise overview of eye tracking systems can be found in "Eye Controlled Media: Present and Future State", Arne John Glenstrup and Theo Engell-Neilson, published by the University of Copenhagen DIKU (Institute of Computer Science) June 1995, viewable at www.diku.dk/~panic/eyegaze/article, and which is incorporated herein by reference.

However, one of the well known problems in using eye motion for controlling wearable computers, wearable cameras, user interfaces and the like, is that calibration of the devices is difficult. The "Eye Controlled Media: Present and Future State" publication referred to herein above lists several problem areas concerned with eye gaze tracking techniques. Known eye gaze tracking techniques suffer from problems concerning head movement, over-sensitive tracking sensors, and equipment that loses calibration easily and quickly.

Several known calibration techniques are used for eye tracking systems as follows:

Local user initiated recalibration: A user makes local recalibration of an eye tracker system by manually moving a mouse pointer across a screen. The user stares at the pointer whilst clicking on the mouse, causing all eye gazes recorded on the vicinity of the point to be calibrated as gazes at the actual point. This calibration system has been used for a corneal/pupil reflection eye tracker.

Local automatic recalibration: This technique is based on the assumption that an "eyecon" having a small black pupil is such an attractive object that a user would not normally look at a point outside the border of the eyecon, but rather straight at the pupil of an eye. When an eye gaze is detected, either outside the eyecon or inside the eyecon, the system performs an automatic recalibration based upon a current tracking data and position of the eyecon assuming a user is looking directly at the pupil of the eyecon.

Reassignment of off-target fixations: Eye gaze fixations which are "reasonably" close to one object and "reasonably" further from all other objects, i.e., not halfway between two objects, are accepted as being on target.

Tracking data tokenization: Raw eye tracking data often contains entirely wrong coordinates, because the tracker has missed a video frame, or a user has blinked, causing discontinuity in data. In a known technique, a series of fixations separated by fast saccades are anticipated, and raw data is fitted to this expected data. Momentary spikes in raw data are interpreted as faulty measurements. A mean gaze position is reported after a short interval (100 ms) is reported as a fixation. The resulting data comprises a string of tokens which describe fixations closer to what the user thinks he/she is fixating, rather than the raw data itself.

Selection prediction using Markov-Chains: A selection prediction algorithm predicts a user's most likely next choice of object in a menu structure using a second order Markov-Chain. The prediction is used to compose a menu that is to be displayed, resulting in a dynamic menu layout system.

Wide angle for locating, tele-lens for tracking: The problems of heavy restrictions on head movement during eye tracking has been addressed by Applied Science Laboratories using an "extended head tracking unit". A system operates simultaneously with two cameras, one with a tele-lens for eye tracking, and one with a wide angle lens to constantly locate and adjust to the user's eye position. One of the cameras locates all the faces in the field of view of a wide angle camera and selects the closest face. This face is continuously tracked using techniques for face color, e.g., skin color, and movement detection, using an artificial neural network which detects the shape of faces. General tracking of face position is combined with specific tracking of eye direction.

Combining tracking from several modalities: In this known technique, data from multiple modes is combined to resolve ambiguities in tracking data. For example, a combination of visual (face) tracking system data and speech recognition system data that is able to "listen" in specific directions greatly improves speech recognition in noisy environments.

Multi-resolution screens for speedy display response: Data in a direction in which a viewer is looking is transmitted with higher resolution than data offset from the direction in which a viewer is looking. The resolution distribution of a transmitted image is dynamically altered accordingly so that a viewer has the impression of looking at a uniformly high resolution image as they scan the image.

General known problems associated with developing eye gaze systems include:

Size and bulkiness of equipment;

Eye tracking equipment is over-sensitive to movement of a user;

Eye tracking equipment currently requires constant user attended recalibration;

Eye tracking equipment must be able to track several persons simultaneously because people work in groups together;

The problem of iris pattern recognition is not solved, and therefore current known eye tracking equipment cannot identify tracked persons;

Eye tracking equipment is not currently personalized enough to store preferences and characteristics of individual user persons.

In many applications having direct commercial potential, such as wearable cameras, users of systems cannot be expected to perform complex calibration methods, but rather to make such applications commercially viable, calibration of eye tracking systems needs to be made simple and automatic, with little or no user input. Consequently, known calibration techniques are difficult to apply to commercially viable products which rely on eye tracking for their control or operation.

Whilst known devices are suitable for laboratory use, they are in general not suited to general mass market consumer applications. In general, they are not easily user wearable, require long training times, and are difficult to calibrate.

SUMMARY

According to a first aspect there is provided a calibration apparatus for automatically self-calibrating a set of eye tracking measurements to a reference space, said apparatus comprising: a tracking device capable of capturing a plurality of eye gaze measurements, representing a plurality of eye gaze positions; a statistical analyzer for determining a statistical distribution of said plurality of eye gaze measurements; a data storage device for storing a predetermined set of statistics data of eye movement measurements; a statistical data comparison component for comparing said statistical distribution data of said plurality of eye gaze measurements with said stored predetermined set of statistical data of eye movement measurements; and a calibration data generating component for generating a calibration data depending upon a result of said comparison.

According to a second aspect there is provided a method of automatic calibration of an eye tracking system, said method comprising: capturing a plurality of eye measurements, wherein each said eye measurement relates to a corresponding eye gaze position of a human eye; determining a set of statistics data from said plurality of eye gaze measurements; comparing said set of statistics of said eye gaze measurements with a set of statistics relating to a plurality of pre-measured eye gaze positions of at least one person; and, as a result of said comparison, determining a calibration correction factor which, when applied to said statistics of said eye gaze measurement, give an optimum match between said statistics of eye gaze measurement and said statistics of predetermined eye gaze positions.

According to a third aspect there is provided a method of automatically calibrating a vision controlled wearable computing entity, said method comprising: capturing a set of eye measurement data corresponding to a plurality of eye movements of a user of said wearable computing entity; determining a characteristic of said set of eye measurements, based upon a statistical analysis of said eye measurement data; comparing said statistical characteristics of said eye measurement data with a set of pre-stored statistical characteristics; and as a result of said comparison, calibrating said set of eye measurements to a predetermined co-ordinate system within which said wearable computing entity and said user have a spatial relationship to each other.

According to a fourth aspect there is provided a method of automatically calibrating a vision controlled computing entity, said method comprising: capturing a set of eye measurements corresponding to a plurality of eye movements of a user of said wearable computing entities; determining a characteristic of said plurality of eye measurements, based upon a statistical analysis of said eye measurement data; comparing said statistical characteristic of said eye measurements with a set of pre-stored statistical characteristics; and as a result of said comparison, calibrating said set of eye measurements to a predetermined co-ordinate system within which said wearable computing entity and said user have a substantially fixed spatial relationship.

Other aspects are as recited in the claims herein.

BRIEF DESCRIPTION OF THE DRAWINGS

For a better understanding of the invention and to show how the same may be carried into effect, there will now be described by way of example only, specific embodiments, methods and processes according to the present invention with reference to the accompanying drawings in which.

DETAILED DESCRIPTION

There will now be described by way of example a specific mode contemplated by the inventors. In the following description numerous specific details are set forth in order to provide a thorough understanding. It will be apparent however, to one skilled in the art, that the present invention may be practiced without limitation to these specific details. In other instances, well known methods and structures have not been described in detail so as not to unnecessarily obscure the description.

In this specification, the term "vision controlled device" is used to mean any vision controlled computer entity which is controlled by a human user's eye movements.

In this specification, the term "wearable computer entity" is used to describe any human portable computer device, including but not limited to wearable cameras.

Figure 1:
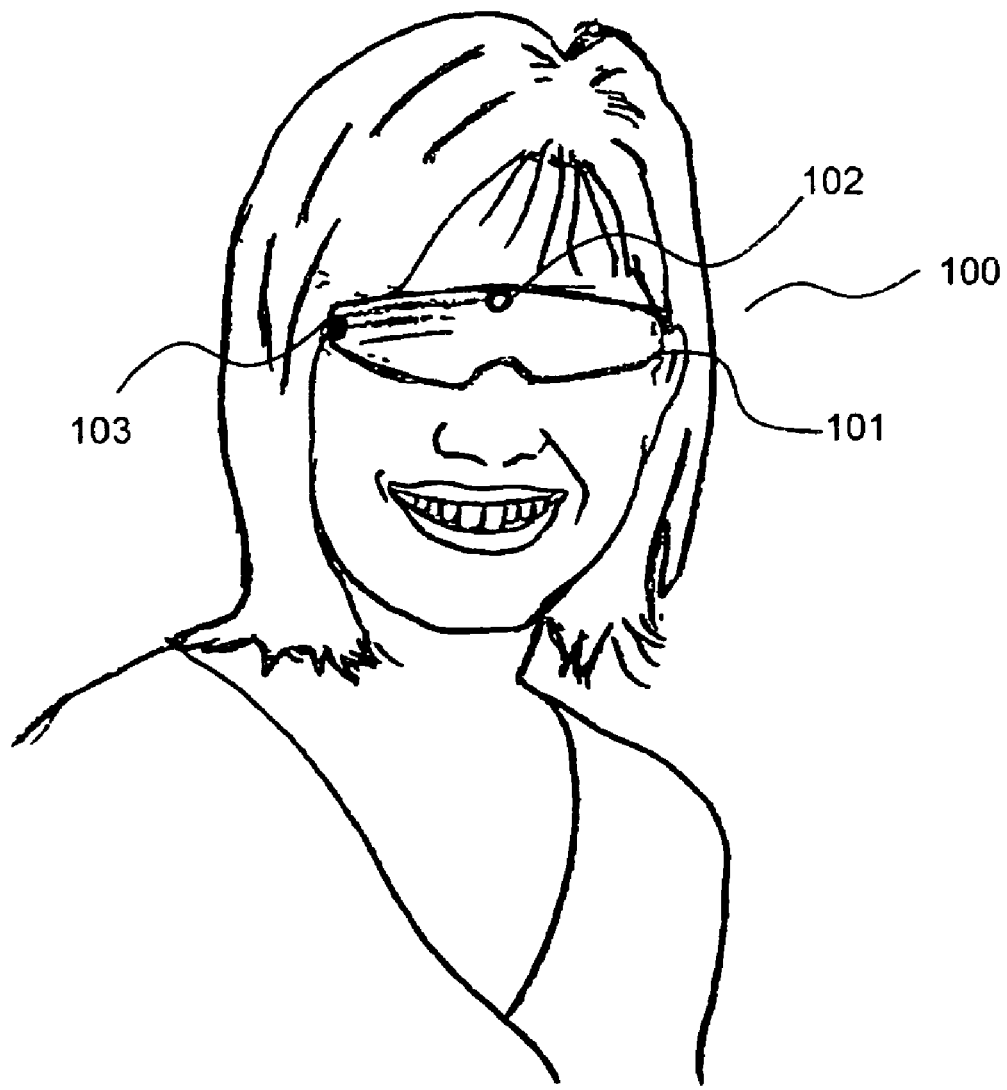
FIG. 1 illustrates schematically one embodiment of a wearable camera device.

Referring to FIG. 1 herein, there is illustrated schematically one example of a vision controlled device, in this case a wearable camera device, incorporated into a headset. The wearable camera device 100 comprises a frame 101 into which is fitted a forward pointing camera 102 for viewing a field of view coincident with an eye gaze direction of a wearer; and an eye tracking device in the form of a tracking camera 103 for tracking eye movements of a wearer of the device. Additionally, an in-built computer device may determine when to capture an image from the main forward looking camera 102, depending upon a level of attention of a user, as determined from the user's eye gaze direction, sensed by the tracking camera 103.

Figure 2:
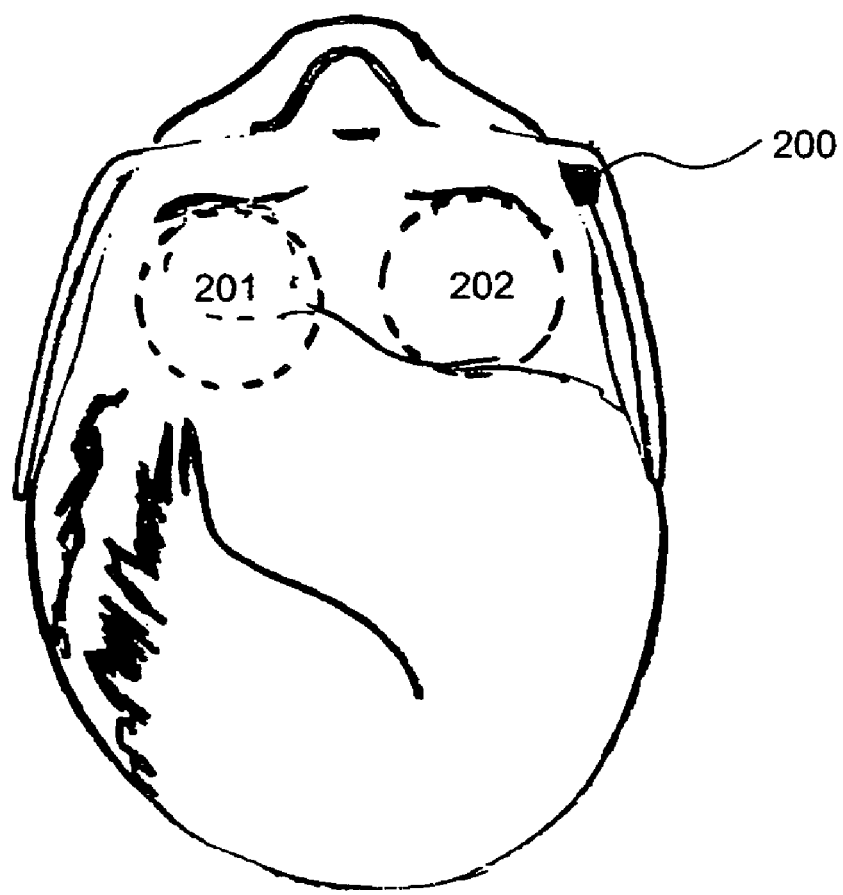
FIG. 2 illustrates schematically in view from above, a layout of the wearable camera device of FIG. 1.

Referring to FIG. 2 herein, there is illustrated schematically in view from above, the wearable camera device as shown in FIG. 1, showing the relative position of tracking camera 200 to the wearer's eyes 201, 202. The tracking camera is aimed to have a field of view across a user's corneal surface. As a user adjusts their direction of gaze, the camera detects movement in the surface of the cornea of the user, which in side profile is not completely spherical, but has a protruding domed shape extending outwardly of the otherwise substantially spherical surface of the user's eye.

For a wearable camera suitable for general consumer use, the camera must be mounted close to a user's body, and in a manner which is as least obtrusive as possible for the user. Similarly, a tracking device (for example an eye tracking camera) must also be mounted close to the user's body so as to be user portable, and be mounted in as unobtrusive a manner as possible in order to find widespread commercial application. In one embodiment, a wearable camera, together with a tracking device may be mounted in a spectacle frame arrangement as illustrated herein with reference to FIGS. 1 and 2.

In the general case of a wearable camera suitable for consumer use, individual persons will have differently shaped heads, and the tracking camera may be placed in an arrangement relative to the user's eyes, which cannot be accurately predicted. Additionally, the mounting for the tracking camera may change with movement of the user and may become readjusted during use, as the user adjusts the frame on which the tracking device is carried. As well as having to accommodate a wide range of different users each having slightly different facial dimensions and head dimensions, the tracking system must be able to accommodate movements in the tracking camera during use, repositioning of the device on the user's head, vibration and wobble.

In situations where the tracking camera is located laterally to the eye as shown in FIGS. 1 and 2, known calibration patterns and methods cannot be used, since many of these rely on either limbus (iris) or pupil tracking from a frontal view, for which direct measurement of the eye gaze direction can be taken. Other prior art methods which rely on Purkinje images, and on multiple reflection of light by the various surfaces of the eye optics are inapplicable where the eye is being viewed laterally from one side.

For a tracking camera displaced laterally at the side of a main gaze direction of a human eye, parameters which can be measured directly and which are related to eye gaze direction include the following:

Tracking of blood vessels in the eye. This gives relative movement of the eye, but no absolute information on eye gaze direction.

Viewed radius of curvature of the cornea. The cornea comprises a parabolic-like surface. Cross-sectional profiles of the cornea when viewed from the side have varying degrees of curvature, which change depending upon the movement of the eye and the gaze direction of the eye.

The inner profile of the iris (partial limbus).

Each of the above measurands bears a direct relationship to a true gaze direction of a person's eye, but are also dependent upon the position of the camera with respect to the gaze direction of the eye. Whilst eye gaze direction is directly related to each one of the above parameters, it is also possible to combine two or more of the above parameters to gain a measure of eye direction. However, there is preferably a calibration of actual eye gaze direction with the measured tracking data in order for the tracking system to work.

Figure 3:
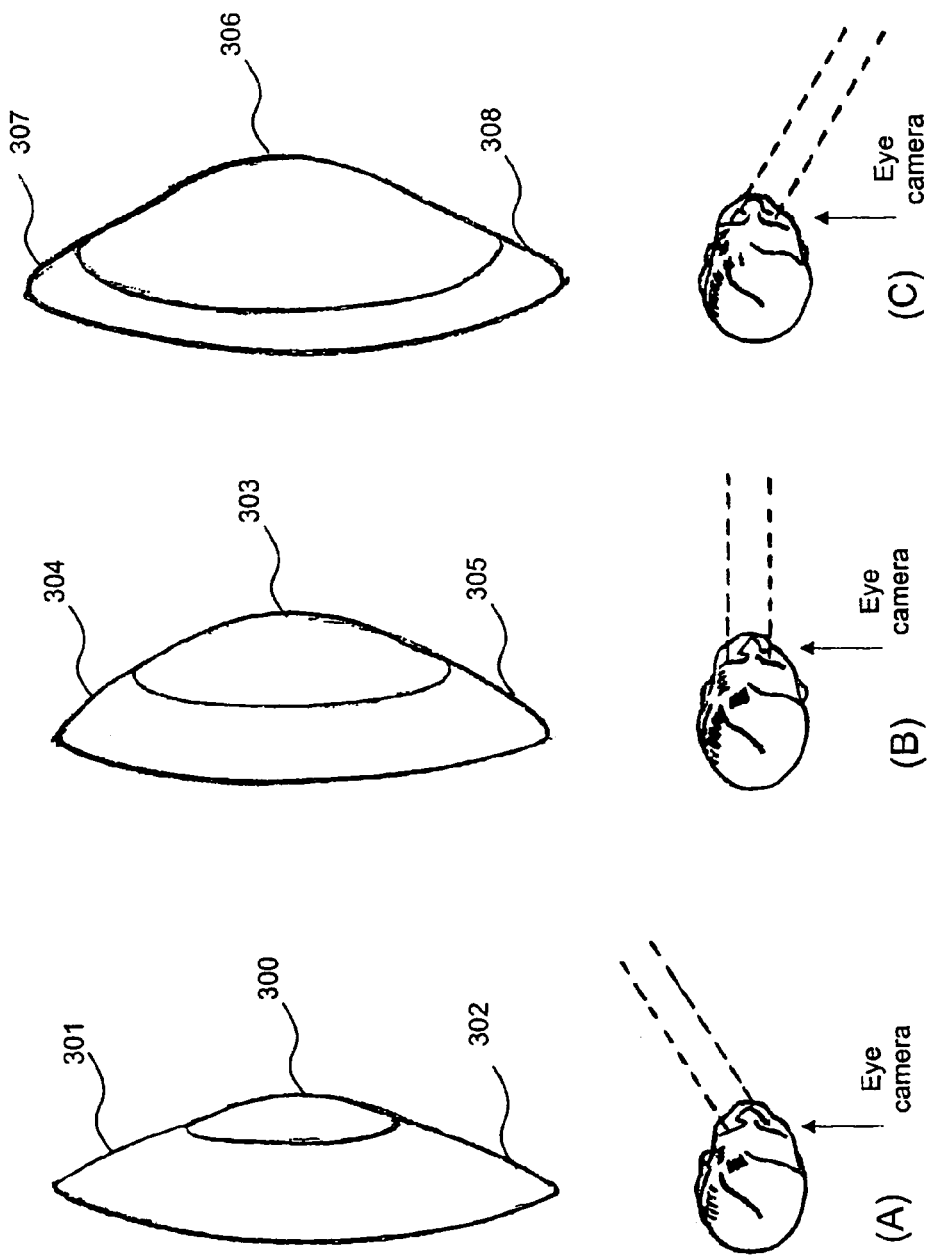
FIG. 3A illustrates schematically a side view of a human eye as viewed by an eye tracking camera positioned laterally to a user, as the user looks to the user's left.
FIG. 3B illustrates schematically a view of a user's eye captured by a tracking camera as a user gazes directly ahead, where the tracking camera is mounted laterally to the user's eye.
FIG. 3C illustrates schematically an image of a user's eye captured by a tracking camera mounted laterally to one side of the user's face as the user views in a right azimuth direction.

Referring to FIG. 3 herein, there is illustrated schematically variations of iris profile as viewed laterally by a tracking camera mounted to one side of a user's head, and pointing in a direction transverse to a main eye gaze direction when a user is viewing straight ahead.

As shown in FIG. 3A, when a user views to their left, in a direction away from the tracking camera, a relatively smaller proportion 300 of iris is visible from the position of the tracking camera, and the overall profile (shown from line 301, 302 in FIG. 3) has a characteristic shape at this angle of view.

Referring to FIG. 3B, when the user gazes directly ahead in a "neutral" stare, a second portion 303 of iris is in view of the tracking camera, and the peripheral profile of the eye extending across the surface of the cornea, (shown as line 304-305 in FIG. 3B) has a second characteristic shape.

Referring to FIG. 3C, when the user gazes in a direction to her right, a third view of the eye is captured by the tracking camera, in which the proportion 306 of viewable iris is relatively larger, and in which the profile of the surface of the eye which can be seen by the tracking camera (lines 307-308 in FIG. 3C) has a third characteristic shape.

In general, for every different eye gaze position, where the user is gazing upwards, to the left, to the right or downwards, or any combination thereof, the tracking camera is able to detect a peripheral profile of the surface of the eye, and a portion of iris is viewed which is unique to that particular eye gaze direction.

Eye tracking devices may track a user's eye movement, either with respect to a user's head, or with respect to a general external environment. Consequently, different types of eye tracking devices may have different frames of reference, referencing eye movements either to a user's anatomy, or to a general environment.

Direct measurements of the eye can be related to an eye gaze direction by using a set of predetermined a priori statistics of eye gaze direction relative to the head of one or more persons to calibrate a set of actual measurements of eye movement taken by a tracking device, for example a tracking camera, and by comparing statistics of the actual measurements of eye movement with the predetermined statistics.

Figure 4:
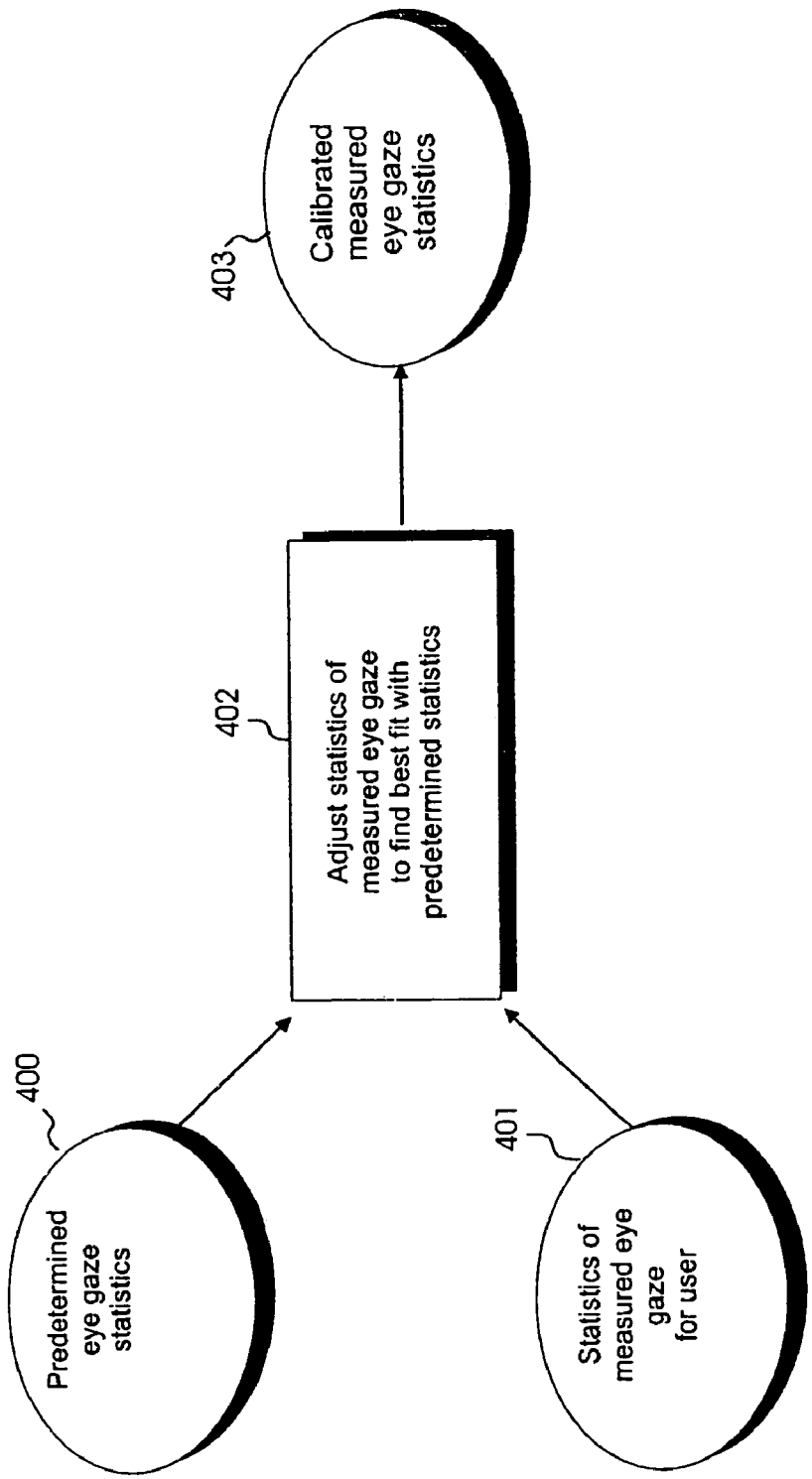
FIG. 4 illustrates schematically a data flow diagram for producing calibration data from a set of predetermined eye gaze position statistics and a set of statistics of measured eye gaze for a user generated by an eye tracking device.

Referring to FIG. 4 herein, there is illustrated schematically a data flow diagram showing data processing to obtain calibrated eye gaze measurements. A set of a priori predetermined eye gaze statistics 400 are pre-stored in a memory device. The predetermined eye gaze statistics may comprise statistics collected from one or a plurality of human individuals, and may therefore represent the "average" eye gaze statistics for a representative sample of humans.

The a priori predetermined statistics for eye movements can be measured under laboratory conditions, and stored as electronic data within a memory of a wearable computing entity. The predetermined statistics may take two forms. Firstly, a set of statistics may be taken for a plurality of persons in order to obtain an "average" statistical information for human users, describing the eye movement patterns of a notional average person. Such statistics are not specific to any one individual person, but may represent a notional average person based upon an average of a test sample comprising a plurality of persons. Secondly, statistics may be derived for measurements taken from just one individual person. In this case, the individual person may have their own particular quirks and idiosyncrasies. Individual statistics may differ from the statistics of a notional "average" person.

Figure 5:
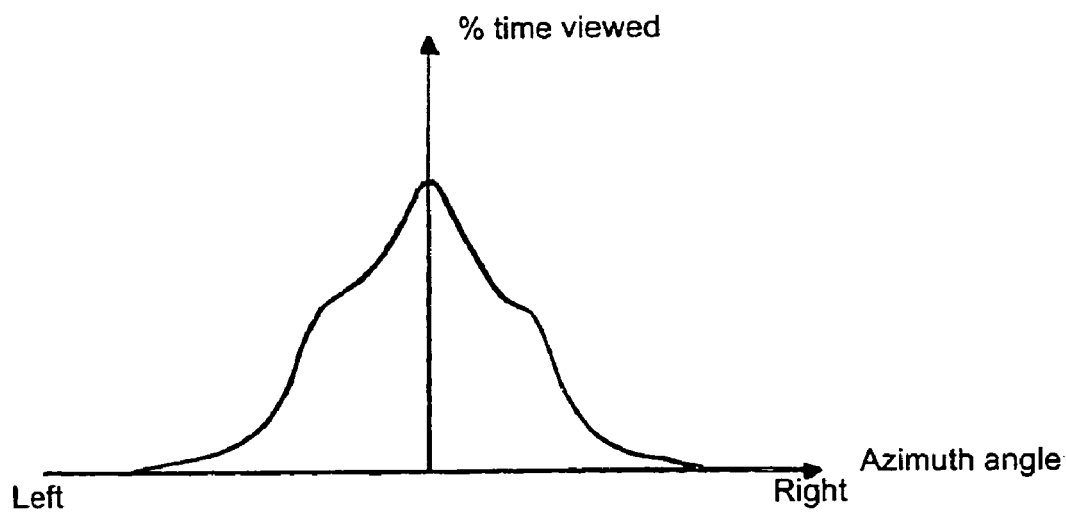
FIG. 5 illustrates schematically one example of a plot of frequency of view, against left and right azimuth determined from a plurality of pre-collected measurements of eye position for one or a plurality of humans.

Referring to FIG. 5 herein, the eye gaze statistics may take the form of digital data representing a curve plotting azimuth angle of gaze relative to a straight ahead "neutral" gaze direction, against a proportion of time spent looking in a particular azimuth angle.

Figure 6:
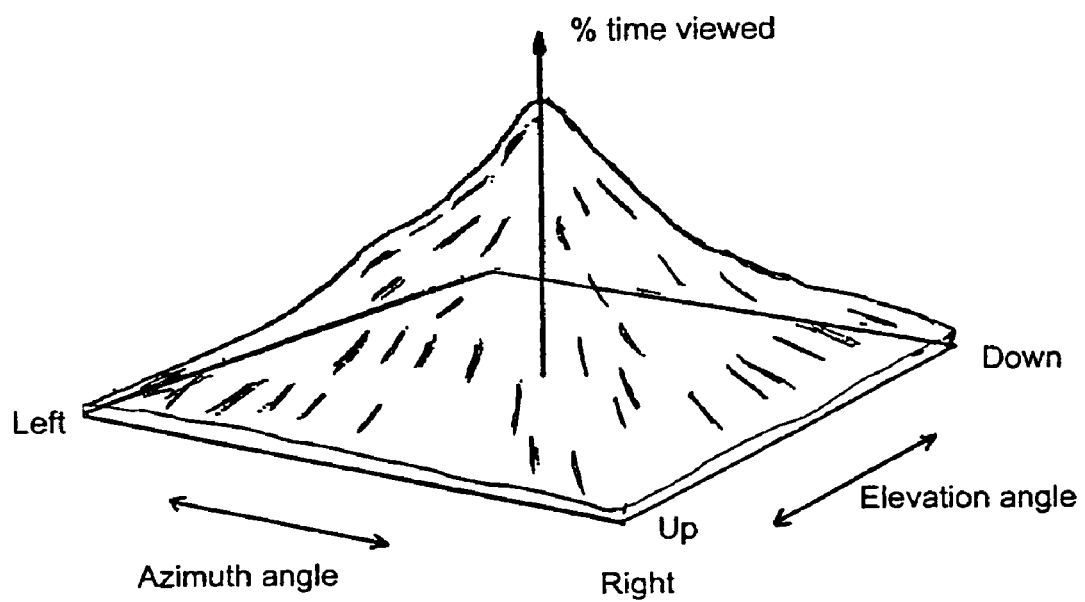
FIG. 6 illustrates schematically a second example of a statistical distribution of measurements of eye gaze position collected from one or a plurality of human users, showing frequency of eye gaze direction in a two coordinate system of azimuth and elevation.

Referring to FIG. 6 herein, in the case of more detailed statistical eye gaze information, the eye gaze statistics may take the form of a three dimensional surface, plotting along a first dimension azimuth angle viewed to the left and to the right relative to a person's straight ahead "neutral" eye gaze direction, and along a second dimension elevation angle viewed upwardly and downwardly, and in a third dimension a percentage occupancy, being a percentage of the time in which the user is looking at a particular azimuth angle and elevation angle, that is a proportion of time in which a person gazes in a particular direction. A mid-point of the azimuth angle and a mid-point of the elevation angle represents the person gazing directly ahead in the neutral gaze direction.

Figure 7:
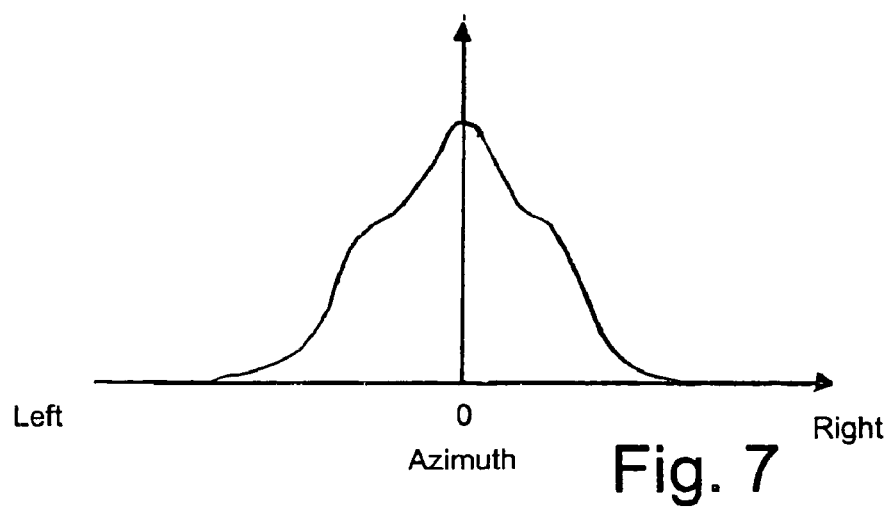
FIG. 7 illustrates schematically a further example of a statistical distribution of a set of predetermined eye position measurements.

Referring to FIG. 7 herein, there is illustrated schematically a plot of an a priori predetermined set of statistics taken for a specimen number of humans, plotting their azimuth eye gaze direction for a predetermined elevation angle against a proportion of time that the person's gaze in that particular azimuth direction. This statistic can be used as a calibration curve for calibrating a set of statistics of measured eye gaze angle as shown in FIG. 8 herein.

Figure 8:
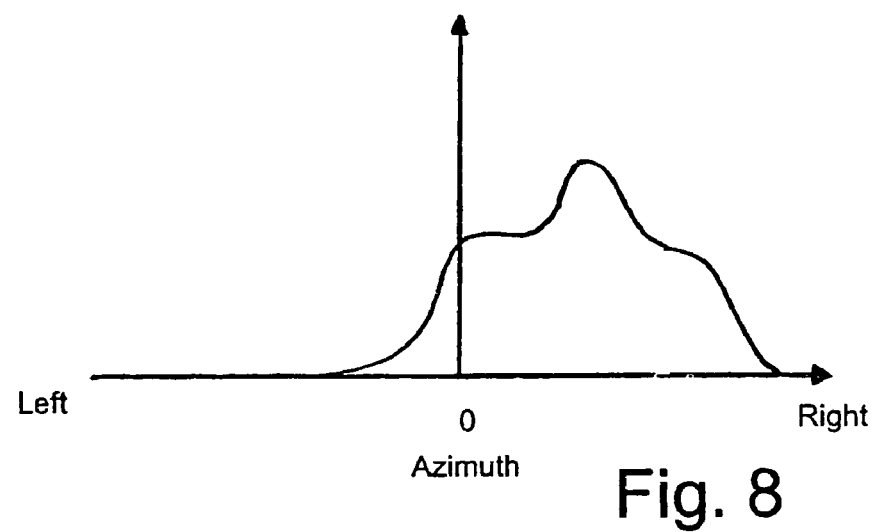
FIG. 8 illustrates schematically a statistical distribution of a set of user eye gaze measurements collected by a tracking device tracking a user's eye movements.

Referring to FIG. 8 herein, there is illustrated schematically a set of uncalibrated statistics of azimuth eye gaze angle for a particular elevation, against a proportion of time spent looking in a particular azimuth angle determined from actual data recorded in real time by a tracking device for an individual user of a wearable camera or wearable computer device. The statistics of measurements of eye gaze direction are taken by an eye tracking device such as an eye tracking camera which views a user's eye from a position worn on the user's body near the eye, for example laterally at one side of the eye.

As can be seen from FIG. 8, a peak of the distribution of eye gaze may not coincide with a nominal central eye gaze direction, indicated by the upright arrow, in the uncalibrated statistical measurements determined from real time measurements of a user's eye gaze.

Figure 9:
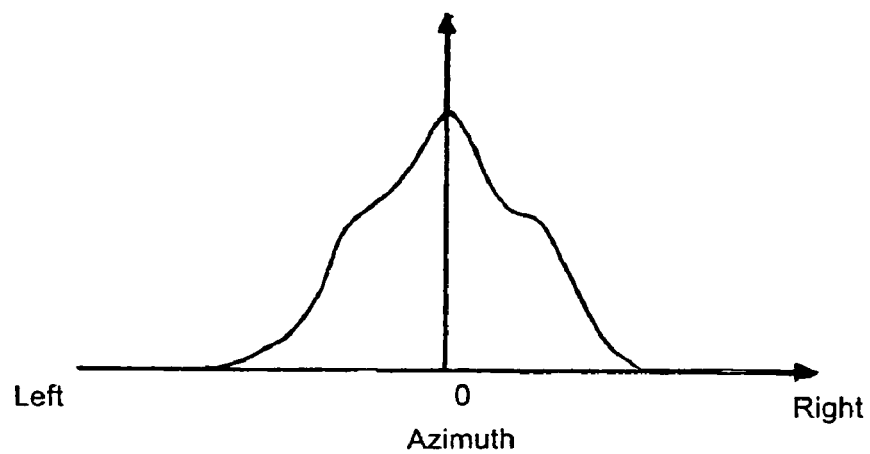
FIG. 9 illustrates schematically the statistical data of FIG. 8, adjusted by a correction factor, to provide a best fit of the statistical data of FIG. 8 to the statistical data of the predetermined set of eye measurements of FIG. 7.

Referring to FIG. 9 herein, there is illustrated schematically the eye gaze measurements curve of FIG. 8, calibrated according to the curve of predetermined statistics shown in FIG. 7 herein. In one method, calibration may occur as follows. The a priori predetermined statistics for azimuth are fitted by a known technique, for example a least squares fit, regression analysis or other line fitting technique to find the closest match with the measured eye statistics of the wearer. The measured eye statistics curve is corrected, by applying a linear translation to the axis of azimuth angle, so that the measured statistics curve of the real time user eye measurements most closely fits the predetermined statistics for eye gaze direction shown in FIG. 7.

Similarly, a corresponding a priori set of predetermined statistic measurements and a set statistics of user eye gaze measurements can be adjusted at each elevation angle, to provide a complete calibration of the real time eye gaze measurements.

Figure 10:
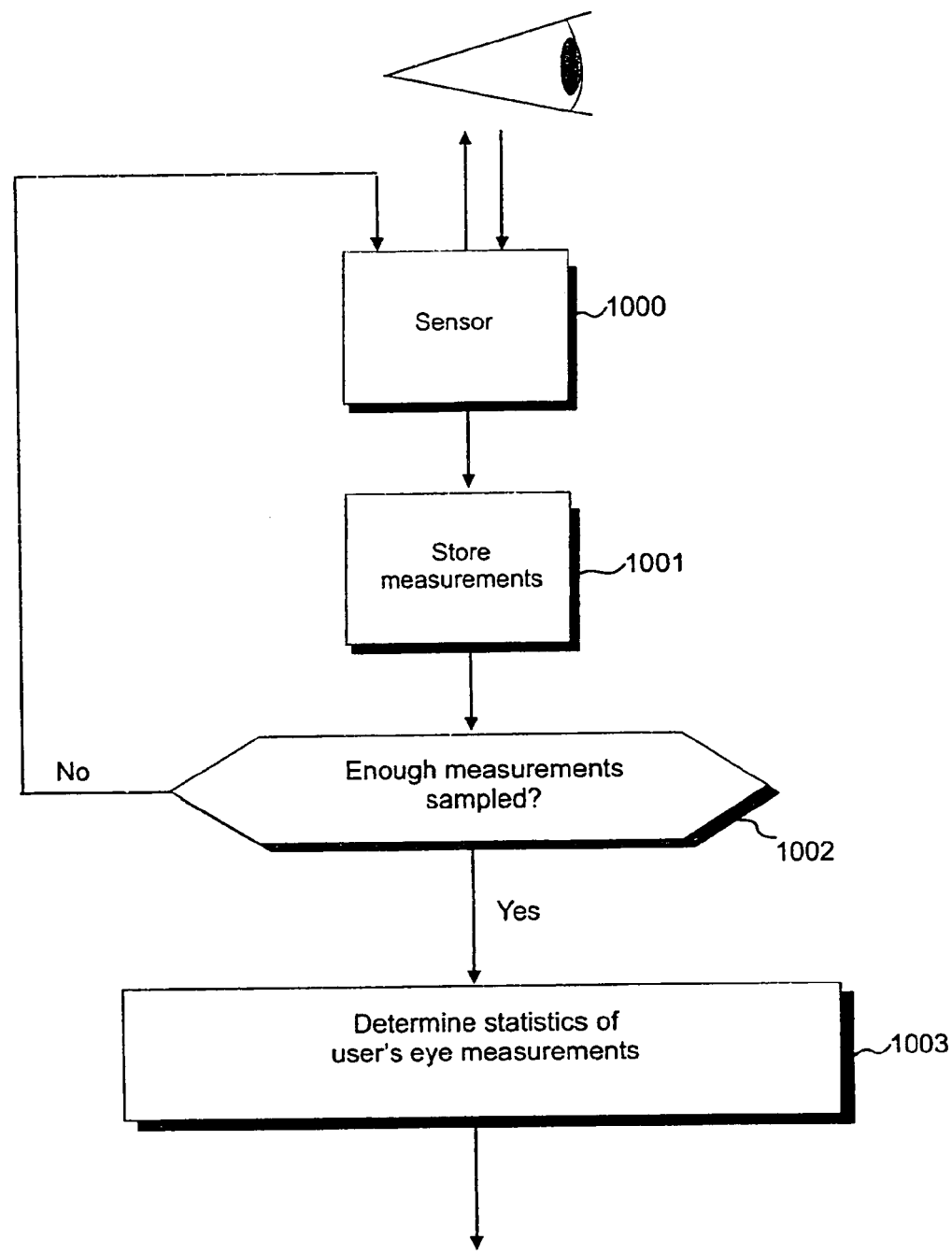
FIG. 10 illustrates schematically components of a self-calibrating eye gaze measurement system.

Referring to FIG. 10 herein, there is illustrated schematically components of a self calibrating vision controlled device comprising signal processing and data processing stages for determining a set of statistics for a user's eye measurements. Eye measurements are recorded by an eye tracking device, denoted sensor 1000 in FIG. 10, which may comprise for example a video camera or other optical detector capable of detecting movements of a user's eye. A physical spatial relationship between the sensor and the user's eye may vary depending upon parameters such as the user's head size, the user's physical facial dimensions, and the placement of the sensor on it's mounting, for example in a spectacle frame-type mounting, in relation to the user's eye. In general, the approximate spatial position of the sensor relative to the user's eye will be known, but there will be variations from user to user in the exact spatial relationship between the user's eye and the eye tracking sensor 1000. In general, a relationship between the eye tracking sensor and a wearable camera may be predetermined, where the eye tracking sensor and the camera are integrated into a same headset, for example in the style of a pair of spectacles to be worn by a user. Eye tracking sensor 1000 repeatedly takes measurements of the eye in order to build up a sufficiently large quantity of measurements that a statistical analysis can be carried out on the eye movement measurements. Individual eye movement measurements are stored in a memory device in process 1001. The memory device is preferably compact portable memory device worn by the user as part of the head set. Eye gaze measurements can take many different forms as described herein before. For example, the eye tracking sensor may record a proportion of visible iris as a series of successive measurements as a user moves their eye gaze around, and/or the eye tracking sensor may take a series of sample measurements of the profile of the eye looking laterally across the corneal surface of the eye, and/or may take sample measurements of the position of blood vessels within the eye which move as the eyeball moves within its socket. Eye tracking sensor 1000 continues to take measurements at predetermined sampling intervals, for example every 0.1 second, 0.2 second, 0.5 second, 0.7 second, 2.0 second or other predetermined interval, until the eye tracking system determines that enough eye measurements have been sampled in process 1002.

In process 1003, a statistical analyzer comprising the tracking system determines a set of statistics of the user's eye measurements. The statistical analyzer may be implemented as a discrete digital signal processing hardware component, or as a general purpose data processor operating in accordance with stored program instructions. A range of known statistic techniques may be used. Statistics of the user's eye movements may be generated in real time, so that a continuously updated stream of statistics of user eye movement is generated by the statistical analyzer. When introduced to a user for a first time, the statistical analyzer may need to receive a large enough sample of user eye measurements from the eye tracking device in order to generate data which is detailed enough to be compared with predetermined eye movement statistics, and this may take a few seconds of operation of the device.

In the best mode herein, as described with reference to FIGS. 4-9 herein, a respective azimuth gaze distribution may be plotted for each individual elevation. Alternatively, a three dimensional surface may be described, having occupancy levels for each gaze direction within a field of view of a user, between extreme left and extreme right azimuth and extreme up and extreme down elevations.

In alternative embodiments, the eye tracking sensor may continue to take further measurements as a background ongoing process. This may be useful if, for example, the relative position of the eye tracking sensor moves with respect to the user's eye after an initial calibration of the system has occurred. Recalibrations may be activated periodically and/or recalibration operations may be carried out over a rolling time window as an ongoing continuous process.

Constant or continuous recalibration may be useful for various reasons. For example, where a user of a wearable computer entity becomes tired over time, their pattern of eye movement behavior may change with the onset of tiredness. Further, a user may readjust the position in which they are wearing a camera to make themselves more comfortable.

Figure 11:
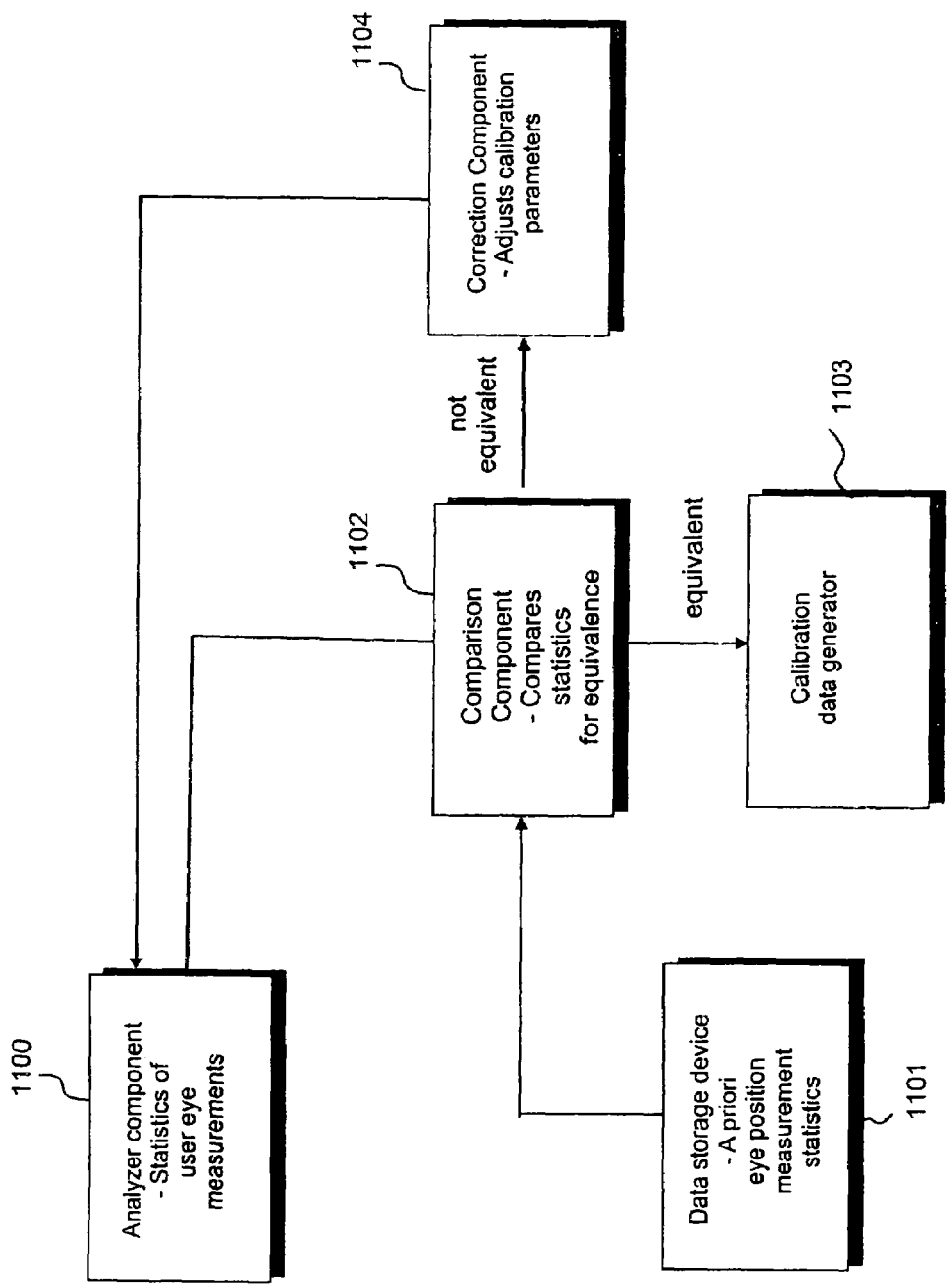
FIG. 11 shows a further set of components of the self-calibrating eye gaze measurement system of FIG. 10 herein.

Referring to FIG. 11 herein, there is illustrated schematically data processing components operable for carrying out an associated data processing method for calibrating a set of collected statistics of user eye measurements against a set of a priori statistics taken from predetermined sample of eye gaze movements of one or a plurality of humans. The statistics of the user eye measurements 1100 generated by the statistical analyzer component are compared with the a priori eye statistics 1101 stored in the data storage device by a comparison component 1102. The comparison component 1102 may comprise a specifically designed digital hardware data processing component or in other embodiments, may comprise a general purpose data processor operating in accordance with stored program instructions. The user eye measurement statistics and the a priori eye position statistics may be compared by a range of known techniques. In one embodiment, curves of occupancy level (percentage time occupying a particular direction) against azimuth may be compared by known curve fitting algorithms, e.g., least squares fit, regression analysis or the like. In other embodiments, three dimensional surfaces of each of the user eye measurement statistics and the a priori eye position statistics may be compared and matched using known surface fitting algorithms.

By fitting the statistics for the user eye measurements to the a priori eye position statistics, a calibration data may be obtained, being the amount of shift or translation needed to be applied to the eye measurement statistics in order to match them with the a priori eye position statistics. The calibration data may take the form of a three dimensional translation which can be applied to eye measurements taken by the eye tracking device, such that the peak of the statistical distribution of eye gaze measurements coincides with a straight ahead eye gaze relative to the user's face.

The comparison component generates a data output which is received by a calibration data generating component 1103, which operates to generate calibration data where the statistics for the user eye measurements are adequately matched to the a priori predetermined statistics of eye movements. The calibration data generating component 1103 may send the calibration data to another component of the vision controlled device which calibrates the raw eye movement data generated by the eye tracking device and corrects the raw eye data to match a true gaze direction of the user. The comparison component also sends data to a calibration correction component 1104. The correction component 1104 adjusts the user eye measurement eye statistics, applying correction factors to those statistics in order to obtain a best fit of the statistics of the user eye measurements to the a priori eye position statistics.

Specific embodiments and methods described herein may be capable of catering for situations where explicit calibration processes are inappropriate, and the calibration is parametric.

Specific embodiments and methods described herein may be capable of being operable in situations where constant and continuous calibration and recalibration of an eye movement tracking device need to be performed because of platform instabilities, for example relative movement of a wearable computing entity and/or wearable camera with respect to a user. The embodiments and methods may be applicable in situations where even if a proper calibration is performed at the outset, the calibration would no longer be valid after a period of time.

Specific embodiments and methods described herein may be capable of providing a way of adjusting default parameters for small changes in mounting of a wearable computer entity or camera device due to different mountings of tracking sensors, different physical configurations of faces and eye sockets of different users.

Specific embodiments described herein may allow calibration of a wearable computing entity for a wide range of human beings having slightly different facial features and different anatomical dimensions and different eye movement behavior.

What is claimed is:

1. A calibration apparatus for automatically self-calibrating a set of eye tracking measurements to a reference space, said apparatus comprising:
   a tracking device capable of capturing a plurality of eye gaze measurements of a side view of an eye of a human subject, representing a plurality of eye gaze positions;
   a statistical analyzer for determining a statistical distribution of said plurality of eye gaze measurements;
   a data storage device for storing a predetermined set of statistics data of eye movement measurements;
   a statistical data comparison component for comparing said statistical distribution data of said plurality of eye gaze measurements with said stored predetermined set of statistical data of eye movement measurements; and
   a calibration data generating component for generating a calibration data depending upon a result of said comparison.

2. The calibration apparatus as claimed in claim 1, further comprising: means for applying said calibration data to said eye gaze measurements, to obtain calibrated eye gaze measurements.

3. The calibration apparatus as claimed in claim 1, wherein said tracking device comprises a digital camera.

4. The calibration apparatus as claimed in claim 1, wherein said eye gaze measurements comprises a set of images of a cornea of the human subject.

5. The calibration apparatus as claimed in claim 1, wherein said eye gaze measurements comprise a set of images of blood vessels of a human eye.

6. The calibration apparatus as claimed in claim 1, wherein said eye gaze measurements comprise a set of measurements of an iris of a human eye.

7. The calibration apparatus as claimed in claim 1, wherein said eye gaze measurements comprise a plurality of digital images of a human eye, said plurality of digital images being captured over a plurality of regularly spaced time intervals.

8. The calibration apparatus as claimed in claim 1, wherein said tracking device comprises a camera that is located laterally to a human eye from which the eye gaze measurements are captured by the camera.

9. A method of automatic calibration of an eye tracking system, said method comprising:
- capturing a plurality of eye gaze measurements of a side view of a human eye, wherein each said eye measurement relates to a corresponding eye gaze position of the human eye;
- determining a set of statistics data from said plurality of eye gaze measurements;
- comparing said set of statistics data of said eye gaze measurements with a set of statistics relating to a plurality of pre-measured eye gaze positions of at least one person; and
- as a result of said comparison, determining a calibration correction factor which, when applied to said statistics of said eye gaze measurement, gives an optimum match between said statistics of eye gaze measurements and said statistics of predetermined eye gaze positions.

10. The method as claimed in claim 9, further comprising: applying said calibration factor to said plurality of eye gaze measurements to calibrate said plurality of said eye gaze measurements into a three dimensional spatial reference system.

11. The method as claimed in claim 9, wherein said statistics of eye gaze measurements comprise data describing a relative frequency of gazing in a particular azimuth direction.

12. The method as claimed in claim 9, wherein said statistics of eye gaze measurements comprise a frequency of an eye gazing in a particular direction in three dimensional space.

13. The method as claimed in claim 9, wherein said statistics of eye gaze measurements comprise data describing a frequency of gazing in a particular direction referenced to a co-ordinate system fixed about a human head.

14. The method as claimed in claim 9, wherein the eye gaze measurements are captured by a camera located laterally to a human eye that is being measured.

15. A method of automatically calibrating a vision controlled wearable computing entity, said method comprising:
- capturing a set of eye measurement data of a side view of an eye of a user corresponding to a plurality of eye movements of the user of said wearable computing entity;
- determining a characteristic of said set of eye measurements, based upon a statistical analysis of said eye measurement data;
- comparing said statistical characteristics of said eye measurement data with a set of pre-stored statistical characteristics; and
- as a result of said comparison, calibrating said set of eye measurements to a predetermined co-ordinate system within which said wearable computing entity and said user have a spatial relationship to each other.

16. A method of automatically calibrating a vision controlled wearable computing entity, said method comprising:
- capturing a set of eye measurement data of a side view of an eye of a user corresponding to a plurality of eye movements of the user of said wearable computing entity;
- determining a characteristic of said plurality of eye measurements, based upon a statistical analysis of said eye measurement data;
- comparing said statistical characteristic of said eye measurements with a set of pre-stored statistical characteristics; and
- as a result of said comparison, calibrating said set of eye measurements to a predetermined co-ordinate system within which said wearable computing entity and said user have a substantially fixed spatial relationship.

17. The method as claimed in claim 16, wherein the eye measurements are captured by a camera located laterally to an eye of the user that is being measured.

18. A calibration apparatus for automatically self-calibrating a set of eye tracking measurements to a reference space, said apparatus comprising:
- means capable of capturing a plurality of eye gaze measurements of a side view of a human eye, representing a plurality of eye gaze positions;
- means for determining a statistical distribution of said plurality of eye gaze measurements;
- means for storing a predetermined set of statistics data of eye movement measurements;
- means for comparing said statistical distribution data of said plurality of eye gaze measurements with said stored predetermined set of statistical data of eye movement measurements; and
- means for generating a calibration data depending upon a result of said comparison.

19. The system of claim 18, wherein the eye gaze measurements are captured by a camera located laterally to a human eye that is being measured.

* * * * *